United States Patent [19]

Michel

[11] Patent Number: 5,383,865
[45] Date of Patent: Jan. 24, 1995

[54] MEDICATION DISPENSING DEVICE

[75] Inventor: Peter Michel, Burgdorf, Switzerland

[73] Assignee: Eli Lilly and Company, Indianapolis, Ind.

[21] Appl. No.: 31,595

[22] Filed: Mar. 15, 1993

[51] Int. Cl.⁶ .............................................. A61M 5/00
[52] U.S. Cl. .................................. 604/232; 604/208; 604/209; 604/186
[58] Field of Search ................ 604/232, 218, 220–222, 604/224, 187, 228–229, 206, 209, 236, 248, 71, 72, 208, 186, 65–66, 210–211, 260, 404, 207; 221/2, 3; 222/39, 41, 46, 402.13, 386, 309, 390, 391

[56] References Cited

U.S. PATENT DOCUMENTS

| | | | |
|---|---|---|---|
| 3,002,517 | 10/1961 | Pitton . | |
| 3,613,952 | 10/1971 | Gilmont . | |
| 4,275,729 | 6/1981 | Silver et al. . | |
| 4,312,343 | 1/1982 | Leveen et al. . | |
| 4,413,760 | 11/1983 | Paton | 222/309 |
| 4,498,904 | 2/1985 | Turner et al. | 604/211 |
| 4,583,974 | 4/1986 | Kokernak | 604/211 |
| 4,592,745 | 6/1986 | Rex et al. | 604/211 |
| 4,659,327 | 4/1987 | Bennett et al. | 604/135 |
| 4,710,178 | 12/1987 | Leonard et al. | 604/209 |
| 4,710,179 | 12/1987 | Haber et al. | 604/211 |
| 4,865,591 | 9/1989 | Sams | 604/186 |
| 4,883,472 | 11/1989 | Michel | 604/208 |
| 4,936,833 | 6/1990 | Sams | 604/232 |
| 4,959,056 | 9/1990 | Dombrowski et al. | 604/186 |
| 4,973,318 | 11/1990 | Holm et al. | 604/208 |
| 5,042,977 | 4/1991 | Bechtold et al. | 604/134 |
| 5,092,842 | 3/1992 | Bechtold et al. | 604/135 |
| 5,112,317 | 5/1992 | Michel | 604/208 |
| 5,114,406 | 5/1992 | Gabriel et al. | 604/136 |
| 5,226,895 | 7/1993 | Harris | 604/208 |
| 5,234,136 | 8/1993 | Kopis | 222/391 |
| 5,240,146 | 8/1993 | Smedley et al. | 222/137 |
| 5,279,585 | 1/1994 | Balkwill | 604/207 |
| 5,279,586 | 1/1994 | Balkwill | 604/207 |

FOREIGN PATENT DOCUMENTS

| | | |
|---|---|---|
| 0268191 | 11/1987 | European Pat. Off. . |
| 0293572 | 4/1988 | European Pat. Off. . |
| 0327910 | 1/1989 | European Pat. Off. . |
| 0338806 | 4/1989 | European Pat. Off. .... A61M 5/315 |
| 250467A1 | 10/1987 | Germany . |
| WO87/02895 | 5/1987 | WIPO . |
| WO88/07874 | 10/1988 | WIPO . |
| WO90/09202 | 8/1990 | WIPO ............ A61M 5/24 |
| WO93/07922 | 4/1993 | WIPO ............ A61M 5/315 |
| WO93/16740 | 9/1993 | WIPO . |

OTHER PUBLICATIONS

Bedienungsanleitung, 1990, Instruction Booklet for Use of Optipen.

Primary Examiner—C. Fred Rosenbaum
Assistant Examiner—V. Alexander
Attorney, Agent, or Firm—Baker & Daniels

[57] ABSTRACT

A medication dispensing device comprising a cartridge for containing an injectable product therein and an injector attached to the cartridge. The injector includes a drive mechanism comprising a dosage sleeve having a dosage knob at the proximal end thereof and a threaded rod coupled to the sleeve and axially advanceable into the cartridge upon clockwise rotation of the knob for dialing up a desired dosage to be injected. A ratchet mechanism is disposed in the injector housing and includes a rotatable piece secured to the dosage sleeve for rotation therewith and a locking seat in engagement with the rotatable piece. The ratchet mechanism permits rotational movement of the sleeve in the clockwise direction only. A disengaging mechanism is secured to the housing of the LCD assembly and includes a pin that extends into and engages the rotatable piece of the ratchet mechanism such that axial movement of the pin causes corresponding axial movement of the stationary piece. Upon depressing the outer surface of the disengaging mechanism, the pin and the rotatable piece are moved axially away from the seat sufficiently enough to permit a user to rotate the dosage knob in a counterclockwise direction to accurately dial back an accidental overdose measurement without removing the cartridge from the injector.

16 Claims, 5 Drawing Sheets

MEDICATION DISPENSING DEVICE

BACKGROUND OF THE INVENTION

The present invention relates generally to medical dispensing devices and, more particularly, to an injector pen that permits selectively measured doses to be dispensed.

Patients suffering from diseases such as diabetes must inject themselves several times each day with an insulin solution. Since the volume of insulin solution to be injected varies from injection to injection, it is necessary for such patients to be able to measure a precise volume of insulin. Diabetics have conventionally used a typical syringe for injection of insulin. However, it is difficult to control the operation of the syringe as well as the quantity of drug injected.

In order to permit a diabetic to measure and administer a more accurate and controlled dosage, injector pens have been developed, which enable a particular dosage to be accurately and conveniently measured. Generally, these pens are threaded onto a cartridge having a particular quantity of liquid medication sealed therein. The cartridge includes a plunger and a mechanism for advancing the plunger in the cartridge in such a manner to dispense the medication.

One such pen that has functioned very adequately is the OptiPen®, which is manufactured by Disetronic AG, of Burgdorf, Switzerland, and which is commercially available through Hoechst of Frankfurt, Germany. This pen includes an LCD assembly for conveniently "dialing up" the desired dosage. To use this pen, a release button is actuated in order to unlock the dosage knob and energize the LCD. The old insulin cartridge is removed and a new insulin cartridge is threaded onto the injector housing. The dosage knob is then turned, which sequentially increases the number appearing in the LCD until the desired dosage setting appears on the LCD. Each number on the display represents a predetermined dosage volume, and each turn of the dosage knob causes an audible "click" sound to be heard. Each turn of the dosage knob causes a threaded rod to move forward in the cartridge. Once the desired dosage is obtained, the needle attached to the end of the cartridge is injected into the skin, and the dosage knob is pressed in slowly until it clicks into place, assuring that the desired dosage of insulin has been injected.

Another dispensing assembly is disclosed in U.S. Pat. No. 4,936,833, issued to Sams. This dispenser includes a disengageable drive mechanism, such as a pair of jaws, that is controlled by a rotatable section of the housing that houses the engagement mechanism This "sleeve", when rotated, disengages the pair of jaws from the plunger rod to permit the rod to be moved into its "zero" position. The rod is then set to the desired dosage, causing a push button to become extended. The drive mechanism is then re-engaged with the rod, and the push button is depressed to administer the dose of insulin.

In addition to delivering insulin, mechanical injectors are useful for the delivery of human growth hormone which, like insulin, must be administered periodically. A problem with the OptiPen described above is that it does not permit a user to correct the error of inadvertently dialing up too great an amount of medication to be dispensed. Any resetting of the dosage of this pen would require that the cartridge be removed from the injector, which not only necessitates considerable effort, but more importantly, generally results in inaccurate dosing, especially if a significant dosage has been initially overdialed. As a result, if too great a dosage is dialed up, it is generally necessary to discharge the entire dose and start over. This is quite problematic in the delivery of growth hormone, since growth hormone is tremendously expensive. Accordingly, it is desirable to provide a dispensing device that permits a user to accurately and conveniently correct an overdial situation.

SUMMARY OF THE INVENTION

The present invention overcomes the problems of the prior art by providing a medication dispensing device having a clutch mechanism that is selectively disengageable with the plunger rod in order to permit, in the event of an overdial situation, the dosage knob to be turned in a counterclockwise direction without removing the medication cartridge from the injector assembly, thereby causing the plunger rod to be dialed back toward the injector assembly in increments that may be accurately measured by a visual dosage indicator.

Generally, the present invention provides, in one form thereof, an injector device and a cartridge assembly, having a quantity of liquid medication sealed therein, threaded to the injector. The injector device comprises a threaded rod and a dosage knob coupled to the rod for advancing the rod a set axial distance within the cartridge upon rotation of the knob. Rotation of the dosage knob actuates a visual counter for indicating to the user the number of incremental turns of the knob. The injector includes a clutch mechanism that is engaged upon attaching the cartridge to the injector. This clutch mechanism prevents counterclockwise rotation of the dosage knob. A disengagement mechanism is provided for selectively disengaging the clutch while the cartridge remains attached to the injector. Once disengaged, the dosage knob and threaded rod may be rotated in a counterclockwise direction to correct an inadvertent dosage overdial situation. Rotation of the dosage knob in the counterclockwise direction actuates the LCD assembly in such a manner to cause the visual counter to decrement the dosage setting.

More specifically, the present invention provides, in one form thereof, a clutch mechanism in the form of a ratchet device comprising an axially movable locking seat disposed within a stationary piece and a movable piece. The seat is locked against rotation and has a plurality of pawls that are forced into engagement with the inclined teeth of the movable piece, which is biased in position by a spring. The pawls permit rotation of the teeth in a first direction, but not in a second direction. The movable piece includes a grooved portion therein forming a lip at the end of the movable piece opposite the teeth. The clutch disengaging mechanism includes a pin that rests within the groove. Upon depressing the disengaging mechanism, the pin is forced away from the locking seat and engages the lip to cause the movable piece to overcome the bias of a spring and move away from the seat. Therefore, the teeth of the movable piece are moved out of engagement with the pawls of the seat to permit rotation of the dosage knob in either a clockwise or counterclockwise direction.

An advantage of the injector device of the present invention is that the dosage setting knob can be dialed back while the cartridge is attached to the injector to provide an accurate correction of an overdial situation.

Another advantage of the injector device of the present invention is that the clutch disengaging mechanism must be positively engaged by the user while the dosage knob is being dialed back, thereby preventing an inadvertent dialing back of the knob.

Yet another advantage of the injector device of the present invention is that an LCD display decrements during the dialing back of the dosage to permit the user to accurately reset the desired dosage.

Another advantage of the injector device of the present invention is that the device eliminates the need to dispense an overdialed dose as waste and then set the correct dose.

The present invention, in one form thereof, comprises a medication dispensing device having a cartridge and an injector attached to the cartridge. The cartridge is designed to contain and seal an injectable product therein and includes a plunger. The injector comprises a housing and a drive mechanism disposed in the housing. The drive mechanism comprises a dosage sleeve having a knob at the proximal end thereof and a rod coupled to the sleeve such that upon rotation of the knob, the rod is axially advanceable into the cartridge. Once into the cartridge, the rod engages and axially advances the plunger within the cartridge. A clutch mechanism is disposed in the housing and comprises a rotatable piece that is secured to the dosage sleeve for rotation therewith and a seat housed in a stationary piece in engagement with the rotatable piece. The seat is configured to restrict rotation of the rotatable piece, and hence the dosage knob, to a first direction only. A disengaging mechanism is provided for selectively disengaging the seat from the rotatable piece, thereby permitting rotation of the dosage sleeve in a second and opposite direction while the cartridge is attached to the injector.

In addition, the present invention comprises, in one form thereof, a method for reducing an excess dosage of measured product in a medication dispensing device. The method includes the step of attaching a cartridge containing an injectable product therein to an injector having a dosage knob and an axially advanceable rod. The knob is rotated in a first direction only to cause the rod to axially advance into the cartridge. A clutch deactuating mechanism is then engaged, and thereafter the dosage knob is rotated in a second and opposite direction until the rod has been axially retracted within the cartridge a sufficient distance to obtain a desired dosage to be injected. Then, the clutch deactuating mechanism is released.

DETAILED DESCRIPTION OF THE INVENTION

Figures 1, 2:
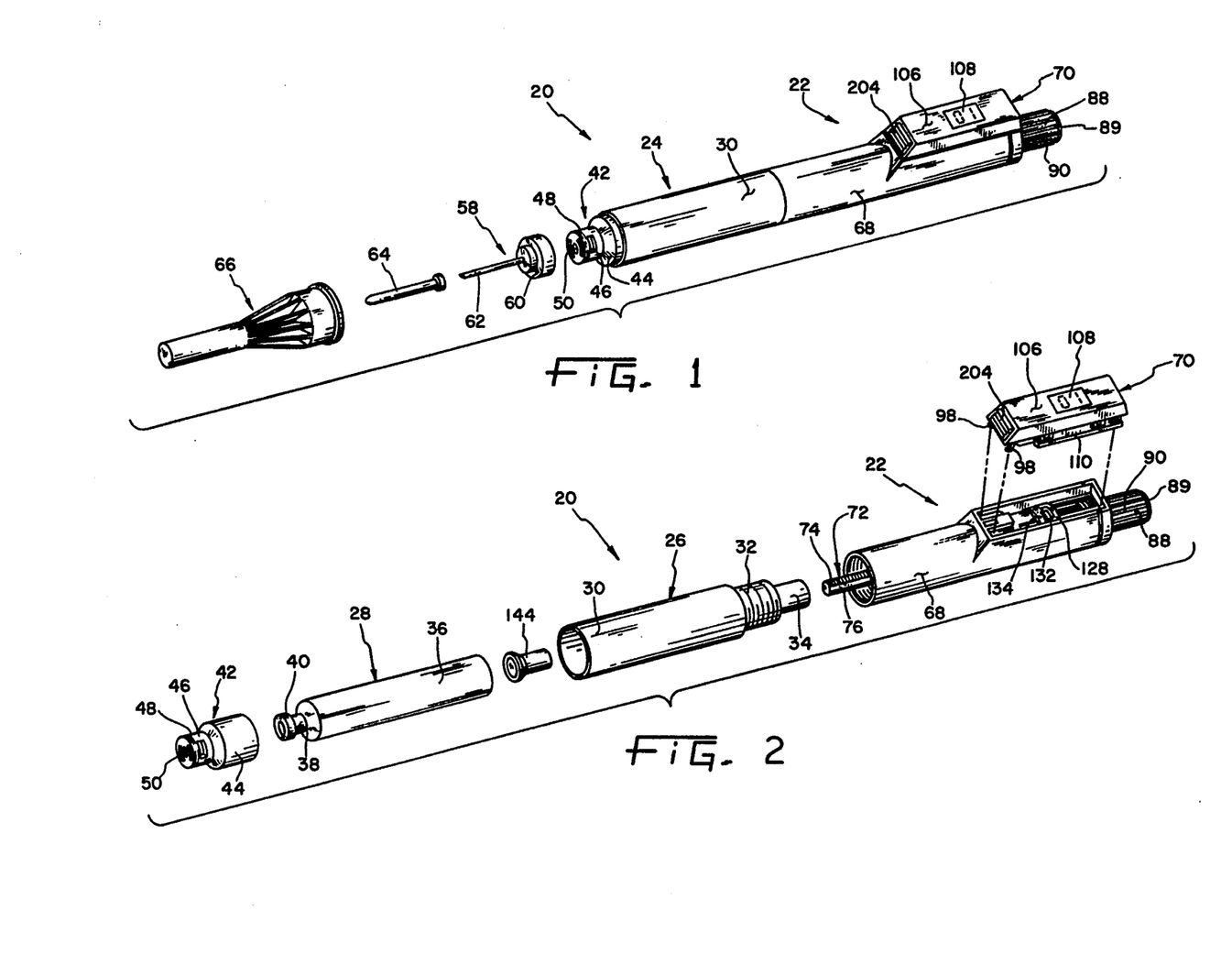
FIG. 1 is a perspective view of an exemplary embodiment of a medication dispensing pen in accordance with the principles of the present invention.
FIG. 2 is an exploded view of the pen of FIG. 1.
Figure 14:
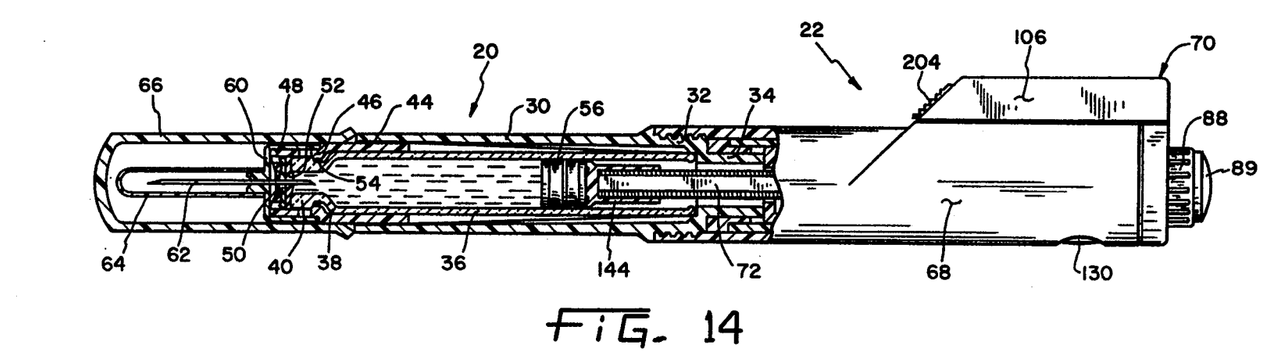

In an exemplary embodiment of the invention as shown in the drawings, and in particular by referring to FIGS. 1 and 2, there is shown a medication dispensing device 20 in the form of a pen. Pen 20 comprises an injector device 22 and a cartridge assembly 24 that is threaded onto injector 22. Cartridge assembly 24 comprises an outer barrel or sleeve 26 and an inner cartridge 28 telescopingly received within barrel 26. Barrel 26 is preferably made of polymethylpentene, which is commercially available from Mitsui Plastics under the trade name "TPX". Barrel 26 comprises a generally cylindrical portion 30, a reduced diameter threaded portion 32 at the proximal end of cylindrical portion 30, and a small cylindrical sleeve portion 34. Cartridge 28 is preferably made of a glass material and is designed to contain the drug to be injected. Cartridge 28 comprises a tubular portion 36, a neck 38, and a lip 40 having a circumferential radius greater than neck 38, as best shown in FIG. 14. In one application of the cartridge, a freeze-dried human growth hormone is placed in tubular portion 36. To preserve the efficacy of the drug, cartridge 28 must be hermetically sealed.

Enclosure cap 42, preferably made of the same material as barrel 26, is designed to fit over cartridge 28 and to provide the appropriate sealing of the contents in cartridge 28. As best shown in FIGS. 2 and 14, cap 42 comprises an enlarged cylindrical portion 44, a reduced diameter portion 46, and a threaded end portion 48. A rubber disc-shaped seal is located within threaded portion 48 and comprises an upper seal portion 50, preferably made of polyisopropylene, and a lower seal portion 52, preferably made of a butyl rubber compound. Cap 42 is secured over the proximal end of cartridge 28 by an interference fit. Cap 42 includes small flexible pawls 54 (FIG. 14) which deform about neck 38 of cartridge 28 and prevent removal of cap 42. As cap 42 is closed about the opening in cartridge 28, seals 50 and 52 seal the proximal end of cartridge 28. A rubber plunger 56 is provided to seal the opposite end of cartridge 28.

As shown in FIG. 1, a needle assembly 58 is provided and includes an internally threaded base 60 that is threaded onto cap 42, and a needle proper 62. Also provided is a needle cover 64 and a protective cap 66.

Further details regarding the cartridge arrangement are found in U.S. Pat. No. 5,334,162, entitled "CARTRIDGE ASSEMBLY FOR A LYOPHILIZED COMPOUND FORMING A DISPOSABLE PORTION OF AN INJECTOR PEN AND METHOD FOR SAME", the disclosure of which being hereby incorporated by reference.

Figure 3:
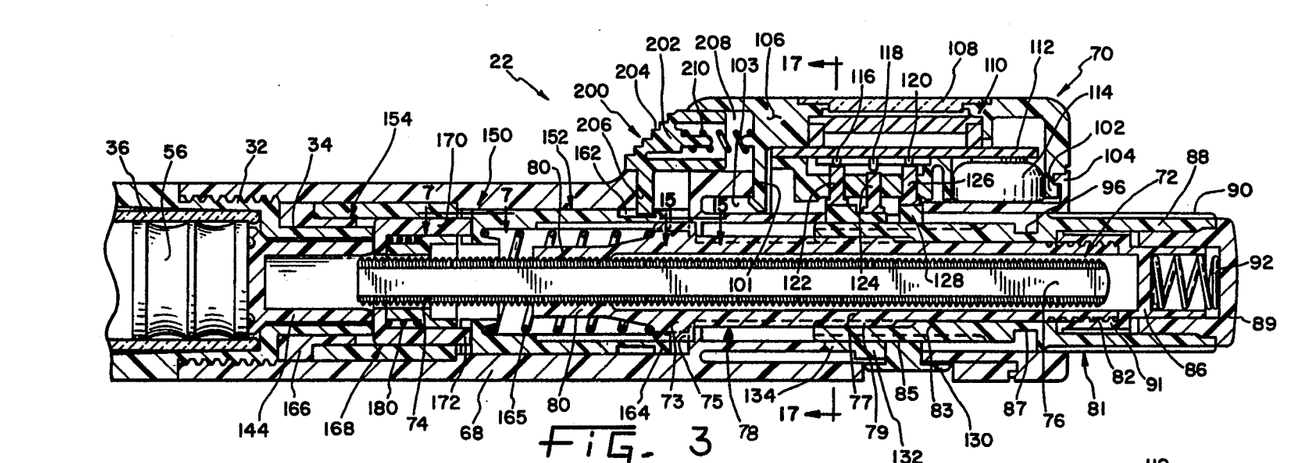
FIG. 3 is an enlarged sectional view of the injector of the pen of FIG. 1, wherein the dosage knob is in its unlocked position.
Figure 4:
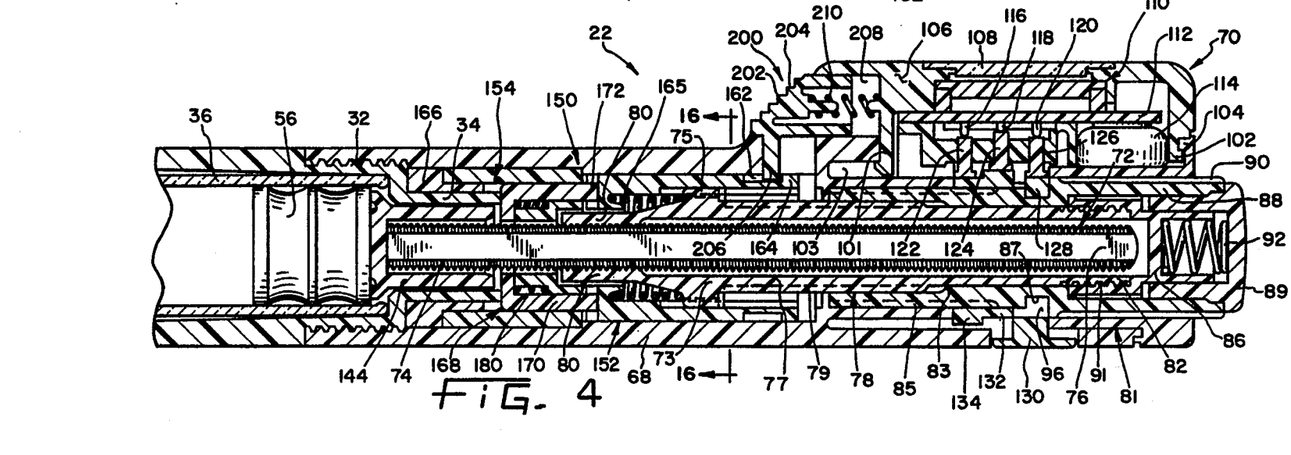
FIG. 4 is a view of FIG. 3, showing the dosage knob in its locked position.

Referring now to FIGS. 3 and 4, there is shown injector 22 in greater detail. Generally, injector 22 comprises an outer plastic housing 68 which houses the working components of the injector, and a dosage mechanism including a liquid crystal display (LCD) assembly 70.

Figure 15:
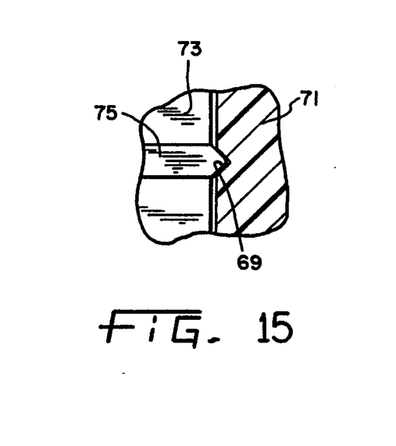
FIG. 15 is an enlarged view, in partial section, of the engagement of the movable member of the clutch mechanism with the inner injector housing of FIG. 3, taken along line 15—15 in FIG. 3.

In order to advance plunger 56 within cartridge 28, a metal rod 72 is provided within injector 22 and is axially movable therein. Rod 72 is threaded throughout the length thereof, as indicated at 74. Rod 72 also includes flats 76 on the surface thereof. Rod 72 is housed within a driving sleeve 78 comprising an internally threaded distal end 80 which engages threads 74 of rod 72, an enlarged diameter portion 73 including ribs 75 formed thereon, a reduced diameter portion 77 having ribs 79 formed thereon, and an externally threaded proximal end 82. As shown in FIG. 15, ribs 75 engage corresponding grooves 69 in internal boss 71 of housing 68. As enlarged diameter portion 73 is rotated with respect to internal housing boss 71, the plurality of ribs 75 periodically engage respective grooves 69, resulting in a slight resistance to further movement, which alerts the user that an incremental dosage has been dialed up or back. Driving sleeve 78 cooperates with an outer sleeve 81. The combination of sleeves 78 and 81 may collectively be referred to as a dosage sleeve. Outer sleeve 81 comprises a tubular portion 83 having ribs 85 extending along the axial length thereof, a reduced diameter surface 87 defining a groove 96 therein, and an enlarged knob portion 88 having ribs 90 thereon. An end cap 89 is ultrasonically welded to knob 88, and a collar 86 is encompassed therein. A spring 92 between end cap 89 and collar 86 permits a slight resiliency of knob 88 while the knob is in its locked position, shown in FIG. 4. Collar 86 includes a threaded portion 91 that engages threads 82 of driving sleeve 78.

LCD assembly 70 is secured to the top of housing 68 by a snap fit. As shown in FIG. 2, assembly 70 comprises a pair of front tangs 98 which engage grooves (not shown) in housing 68 to form an interference fit. Similarly, as shown in FIGS. 3-4, a groove 103 in assembly 70 receives a central tang 101, and a rear tang 102 engages an upwardly extending ear 104, each being a snap fit. Although it is possible that assembly 70 could be removable from housing 68, it is preferable that the snap fit be a permanent connection. Although a snap fit arrangement is preferred, assembly 70 may be secured to housing 68 in any suitable manner, such as by ultrasonic welding.

Figure 17:
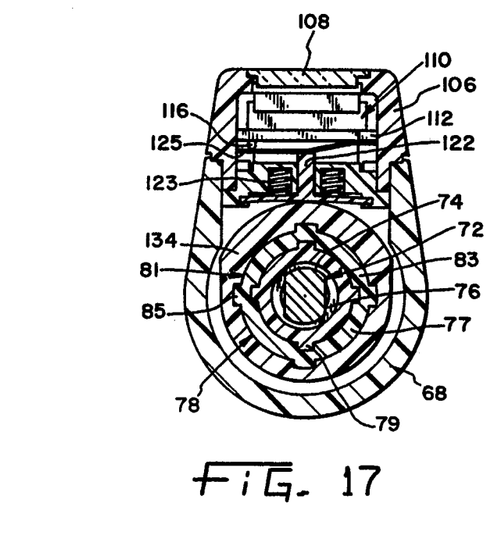
FIG. 17 is an enlarged sectional view of the injector of FIG. 3, taken along line 17—17 in FIG. 3.

Referring to FIGS. 3, 4, and 17, LCD assembly 70 generally comprises a housing 106, a display window 108, a plastic circuit housing 110 that houses an integrated circuit board 112, a battery 114, and a plurality of contacts 116, 118, 120 for actuating the IC circuit in such a manner to alter the display shown in window 108. Each contact is associated with a small plastic rod and strip assembly 122, 124, 126, respectively, via a flexible strip 125 (FIG. 17). Each rod/strip assembly is biased downwardly by a pair of springs 123 (FIG. 17) so that in their biased positions, rod/strip assemblies 122, 124, 126 do not engage contacts 116, 118, 120.

Referring again to FIGS. 3 and 4, a small annular ring 128 is secured to housing 68 and includes a button 130 integral therewith for permitting ring 128 to be moved radially upwardly. However, ring 128 is secured to housing 68 in such a manner that prevents rotational or axial movement of the ring when knob 88 is rotated or pressed in. A rotatable camming mechanism is adjacent ring 128 and comprises a first cam portion 132 and a second cam portion 134. As shown in FIG. 17, cam 134 includes notches therein which receive corresponding ribs 85 of outer sleeve 81 for rotation with sleeve 81. However, the internal notches of cams 132 and 134 permit ribs 85 to slide axially therein so that cams 132 and 134 remain stationary upon axial movement of outer dosage sleeve with respect to injector housing 68.

Figure 8:
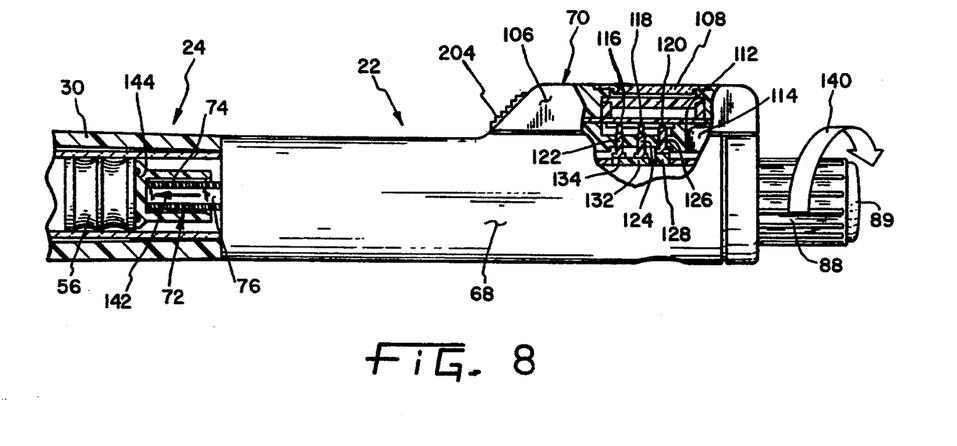
FIG. 8 is an enlarged, fragmentary elevational view of the pen of FIG. 1, particularly showing a portion of the LCD device in section and further showing a portion of the cartridge in section.

Referring again to FIG. 17, there are shown ribs 79 of driving sleeve 78 secured within respective internal notches of outer sleeve 81. Preferably, ribs 79 are secured therein by a friction fit, thereby causing outer sleeve 81 to be movable with driving sleeve 78, both axially and rotatably. Referring to FIG. 8, knob 88 is rotatable in the clockwise direction as indicated by arrow 140. Rotation of knob 88 in this direction causes both outer sleeve 81 and driving sleeve 78 to rotate therewith. Rotation of driving sleeve 78 causes the threads of distal end 80 to engage threads 74 of rod 72, thereby causing the distal end of rod 72 to move axially forward out of injector housing 68, as indicated by direction arrow 142 of FIG. 8. Rod 72 then engages a plastic rod tip 144 within inner cartridge 28 of cartridge assembly 24, which in turn engages plunger 56 and moves it forward in inner cartridge 28. The dosage of drug to be injected is determined by the axial position of plunger 56 within cartridge 28. As plunger 56 is moved forward within inner cartridge 28, the dosage injected is increased.

Figure 7:
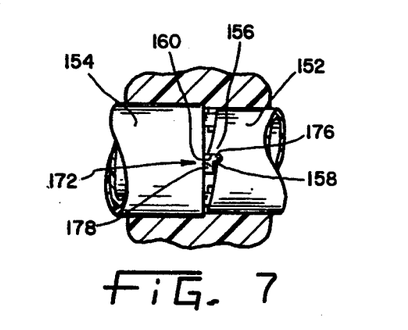
FIG. 7 is an enlarged view, in partial cross-section, of the ratchet engagement between the stationary and movable piece of the clutch mechanism, as shown in FIG. 3, taken along line 7—7 in FIG. 3.
Figure 16:
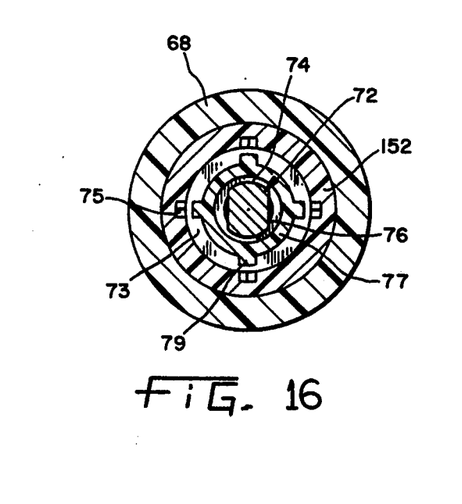
FIG. 16 is an enlarged sectional view of the injector of FIG. 4, taken along line 16—16 in FIG. 4.

Referring again to FIGS. 3 and 4, a clutch mechanism 150 is provided for preventing movement of knob 88 in a counterclockwise locking direction. Clutch 150 comprises a movable piece 152 and an axially movable locking seat 168 disposed within stationary piece 154. Movable piece 152 is generally cylindrical in shape and includes a distal end having a plurality of inclined teeth 156 formed about the circumference thereof, as shown in FIG. 7. Each tooth 156 includes a corresponding groove 158 adjacent a stop surface 160. The opposite (proximal) end of movable piece 152 includes a circumferential groove 162 therein, which defines a lip 164, as shown in FIGS. 3 and 4. A spring 165 is disposed in movable piece 152 to bias piece 152 in a proximal direction. As best shown in FIG. 16, movable piece 152 includes a plurality of circumferentially spaced internal grooves which receive ribs 75 of enlarged diameter portion 73 of sleeve 78. Thus, movable piece 152 is movable with sleeve 78 both axially and rotatably.

Figure 5:
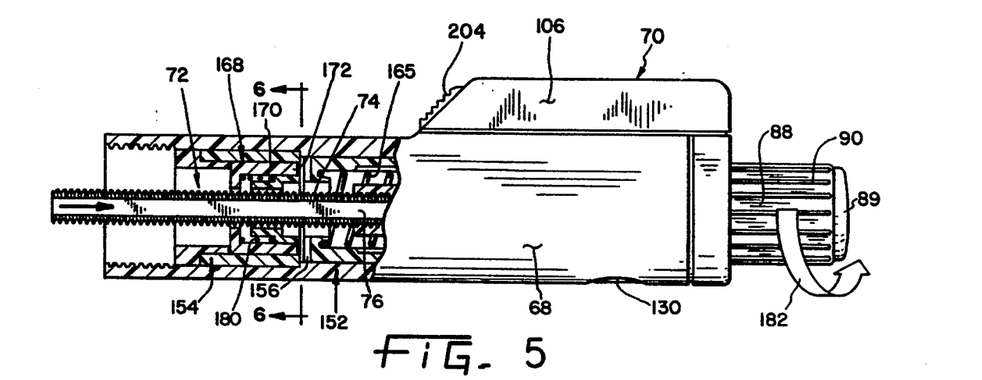
FIG. 5 is an enlarged elevational view of the injector of FIG. 1, particularly showing a portion of the injector in section.
Figure 6:
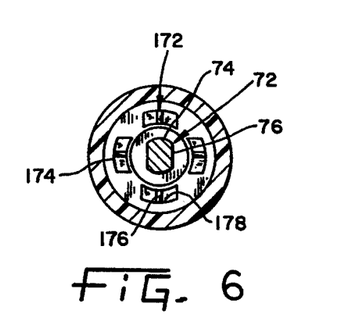
FIG. 6 is an enlarged sectional view of the stationary piece of the clutch mechanism, as shown in FIG. 5, taken along line 6—6 in FIG. 5.

Stationary piece 154 is also generally cylindrical in shape and comprises a distal end 166 having an opening therein for receiving sleeve portion 34 of cartridge barrel 26. As shown in FIGS. 3 and 4, axially movable locking seat 168 is disposed within stationary piece 154 and comprises a plurality of prongs terminating in ends or pawls 172. As shown in FIGS. 6 and 7, pawls 172 are extendable through openings 174 in the proximal end of stationary piece 154. Pawls 172 are generally L-shaped and comprise an extending dog 176 and a base 178. Seat 168 is biased in a retracted position within the cylindrical body of stationary piece 154 by a spring 180, as shown in FIG. 5. Thus, before cartridge 24 is attached to injector 22, there is no engagement between seat 168 and movable piece 152. This permits knob 88 to be rotated in the counterclockwise direction, as shown by arrow 182.

Upon threading cartridge 24 onto injector 22, as shown in FIGS. 3 and 4, sleeve portion 34 of cartridge barrel 26 engages seat 168 overcoming the bias of spring 180 to force seat 168 toward movable piece 152. This forces pawls 172 out of openings 174 and into engagement with the proximal end of movable piece 152. Because pawls 172 extend through openings 174, seat 168 is prevented from rotating. Referring to FIG. 7, each dog 176 is disposed in a corresponding groove 158, forming a ratchet engagement that permits rotation of movable piece 152 in the clockwise direction but prevents rotation in the counterclockwise direction due to the engagement of stop surface 160 with dog 176. Upon clockwise rotation of piece 152, the inclined surface of each tooth 156 slides along respective pawl 172 until groove 158 of the tooth 156 slides over and receives respective dog 176 of the pawl. This engagement results in the characteristic "click" sound upon dialing up the desired dosage.

Referring yet again to FIGS. 3 and 4, there is shown a clutch deactuating mechanism 200 for permitting knob 88 to be rotated in a counterclockwise direction while cartridge 24 is attached to injector 22. Mechanism 200 comprises a main body portion 202 having an outer user-engaging surface or button 204 and a downwardly extending pin 206. Body 202 is disposed in an opening 208 formed in the distal end of LCD housing 106 and is biased by a spring 210 in an outward position. Pin 206 extends through an opening in injector housing 68 and is disposed within groove 162 of movable piece 152.

Figure 9:
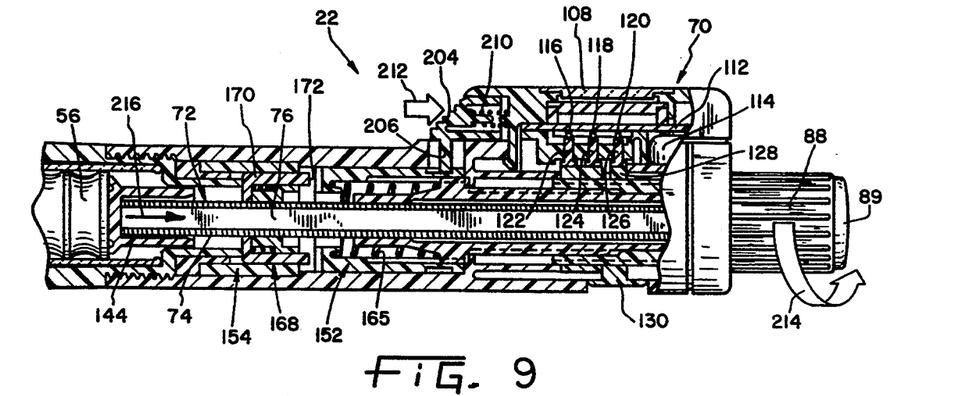
FIG. 9 is a view of FIG. 8, particularly showing most of the injector in section, and further showing the dosage knob being rotated in the counterclockwise direction upon disengagement of the clutch.

Upon depressing button 204, as shown by arrow 212 in FIG. 9, body 202 is forced in a proximal direction against the bias of spring 210. Accordingly, pin 206 is forced against lip 164 of movable piece 152 thereby forcing movable piece 152 away from seat 168, as shown in FIG. 9. Once movable piece 152 is disengaged from seat 168, knob 88 may be turned in the counterclockwise direction as shown by arrow 214. This causes rod 72 to retract toward injector 22, as shown by arrow 216.

In operation, LCD contact 120 functions to actuate and deactuate the LCD assembly. Referring to FIG. 4, dosage knob 90 is in its engaged position, which causes ring 128 to rest within groove 96 of sleeve 81. Rod 126 is not forced against contact 120, resulting in the LCD being in its "off" position. In addition, ring 128 forms an interference fit with groove 96 to overcome the bias of spring 165, which biases dosage knob 88 in its extended position.

Upon depressing reset button 130, ring 128 is forced upwardly and out of groove 96, thereby permitting spring 165 to move sleeve 94 and knob 88 into its extended position shown in FIG. 3. At this point, ring 128 rests upon a longitudinal rib 85 of outer sleeve 81, which exerts a force on rod/strip 126 sufficient to overcome the bias of the small spring force. Rod 126, in turn, exerts a force on contact 118, which actuates the LCD.

Figure 10:
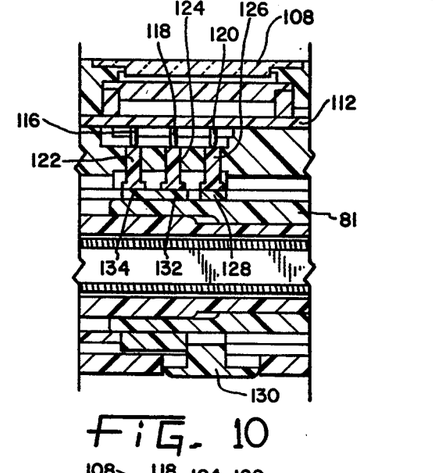
FIGS. 10-14 are each enlarged, fragmentary, sectional views of the LCD device of the pen of FIG. 1, particularly showing the different cam positions as a result of rotation of the dosage knob.

Referring now to FIGS. 10-13, there is shown a cam configuration of an exemplary embodiment. However, other cam configurations are possible. In FIG. 10, the LCD is in its "off" position with ring 128 being retained within groove 96. Each cam surface 132 and 134 is circular in cross section and comprises a raised surface over about half its circumference and a lowered surface over the remaining half. However, the raised and lowered surfaces of each cam are offset (e.g. 90°) with respect to one another resulting in different combined geometric configurations throughout their circumferences.

Figure 11:
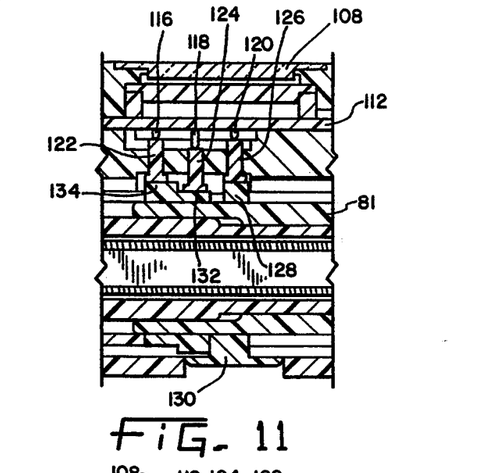
Figure 12:
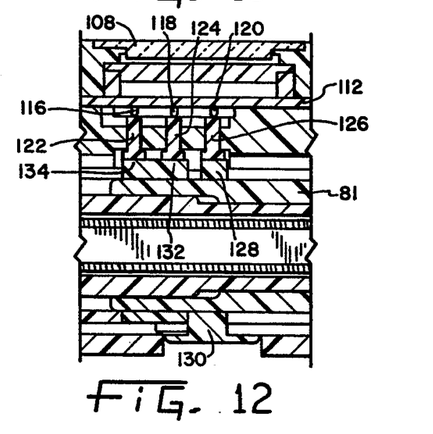
Figure 13:
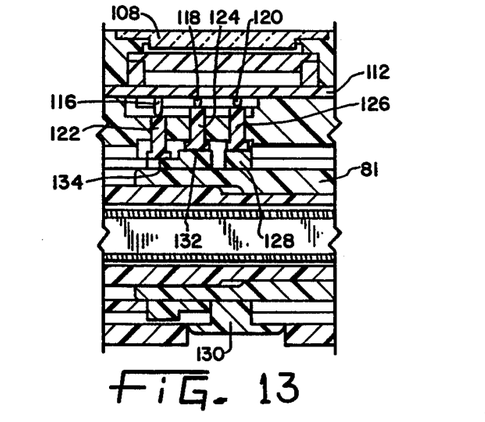

Referring to FIG. 10, both cams 132 and 134 are shown with their reduced surfaces adjacent rods 124 and 122, respectively. As a result, neither rod depresses its respective contact. In FIG. 11, the LCD display has been actuated, and dosage knob 88 has been turned a quarter turn. As a result of the rotation, a new cam configuration is achieved, wherein cam 134 is raised, and cam 132 is lowered. Consequently, contact 116 is engaged, while contact 118 remains nonengaged. This different contact configuration causes the number shown in LCD window 108 to be incremented by one. As knob 88 is turned another quarter turn, yet another cam configuration of FIG. 12 is shown, wherein the raised surfaces of both cams 132 and 134 are in engagement with contacts 118, 116, respectively. Again, this new contact configuration causes the number shown in LCD window 108 to be incremented by one. Finally, as shown in FIG. 13, knob 88 is turned yet another quarter turn, resulting in a lowered cam surface 134 and a raised cam surface 132. As a result, contact 116 is not depressed, while contact 118 is depressed. This new contact configuration causes the number shown in the LCD window 108 to be incremented yet again.

As shall be discussed hereinafter, the present invention provides a mechanism that permits knob 88 to be turned in an opposite direction while the cartridge is attached to the injector. If knob 88 is turned back on quarter turn from its position of FIG. 13 to its position of FIG. 12, the contact configuration is altered from only contact 118 being depressed to both contacts 116, 118 being depressed. This change is sensed by the IC circuit to cause the number appearing in window 108 to be deincremented by one. It is understood that a variety of possible geometric variations are possible to achieve the desired results, and that the particular cam configuration shown in FIGS. 10-13 is only one possible arrangement.

As dosage knob 88 is rotated clockwise, rod 72 is moved toward cartridge 24 to measure a desired dosage to be injected, as described previously. In the event that the user inadvertently turns knob 92 too far in the clockwise direction, e.g. ten increments instead of eight, as indicated by the LCD display, it will be necessary to dial back the dosage, e.g. two increments. In order to do this, button 204 is depressed as shown in FIG. 9, thereby disengaging the clutch mechanism, and knob 88 is turned back in the counterclockwise direction the desired number of increments (e.g., two) as would be indicated on the LCD display. Button 204 must remain pressed while knob 88 is moved in the counterclockwise direction. Once the desired dosage has been set, button 204 is released, thereby reengaging the clutch mechanism. Then, knob 88 is pressed to its position shown in FIG. 4 in order to inject the proper dosage of drug into the patient.

Although a particular type of clutch mechanism has been shown, any type of coupling device may be employed in order to prevent counterclockwise movement of knob 88 while the cartridge is attached to the injector. Likewise, any clutch deactivating mechanism may be utilized to permit the dosage knob to be dialed back upon an overdial situation while the cartridge remains attached to the injector.

It will be appreciated that the foregoing is presented by way of illustration only, and not by way of any limitation, and that various alternatives and modifications may be made to the illustrated embodiment without departing from the spirit and scope of the invention.

What is claimed is:

1. A medication dispensing device, comprising:
   a cartridge for containing and sealing an injectable product therein, said cartridge including a plunger therein; and
   an injector attached to said cartridge and comprising a housing, a drive mechanism disposed in said housing and including a dosage sleeve having a knob at a proximal end of said dosage sleeve and a rod coupled to said sleeve such that upon rotation of said knob, said rod is axially advanceable a first distance to establish a set dosage of injectable product to be delivered without effecting delivery of the injectable product, a clutch mechanism disposed in said housing and comprising a rotatable piece that is secured to said dosage sleeve for rotation therewith and a locking seat in engagement with said rotatable piece and being configured to restrict rotation of said rotatable piece, and hence said dosage knob, to a first direction only, a disengaging mechanism for selectively disengaging said locking seat from said rotatable piece thereby permitting rotation of said dosage sleeve in a second and opposite direction while said cartridge is attached to said injector to reduce the first distance of axial advancement of said rod thereby reducing the set dosage of injectable product to be delivered, wherein said rod is axially advanceable a second distance upon axial force being applied to said knob to engage and axially advance said plunger to effect delivery of the set dosage of injectable product.

2. The device of claim 1, wherein said rotatable piece includes a grooved surface therein defining an adjacent lip, and said disengaging mechanism comprises a pin disposed in said grooved surface in such a manner that axial movement of said pin causes said pin to engage said lip, thereby causing axial movement of said rotatable piece away from said locking seat.

3. The device of claim 1, wherein said rotatable piece is generally tubular in shape and includes a spring therein for biasing said rotatable piece against said locking seat.

4. The device of claim 1, wherein a liquid crystal display (LCD) housing is secured to said injector housing and contains an LCD assembly therein including an integrated circuit, a contact for periodically inputting a signal to the circuit, and a display window for providing a visual display of the output delivered by the circuit, wherein the contact is configured to be periodically engaged by said dosage knob to cause a dosage indicia to appear in the display window.

5. The device of claim 4, wherein said disengaging mechanism is secured to said LCD housing and includes a pin extending through an opening in said injector housing and engaging said rotatable piece.

6. The device of claim 1, wherein said clutch mechanism is in the form of a ratchet device.

7. The device of claim 1, wherein the rod is advanceable by means of a threaded connection between said rod and said sleeve.

8. The device of claim 1, including a display means operatively connected to said sleeve for providing a visual dosage indication that increments-and decrements as said sleeve rotates respectively in the first and second directions.

9. The device of claim 1, wherein said disengaging mechanism includes a user actuated element that is connected to said clutch to disengage said seat and rotatable piece when said element is actuated.

10. The device of claim 9, wherein said user actuated element is slidable relative to said housing.

11. A medication dispensing device, comprising:
    a cartridge for containing and sealing an injectable product therein, said cartridge including a plunger therein; and
    injector means attached to said cartridge for delivering a desired dosage of product into a patient, said injector means including knob means for engagement by a user and a rod coupled to said knob means, said rod being axially advanceable with respect to said housing upon rotation of said knob means in a first direction, wherein said rod is advanceable a first distance to establish a set dosage of injectable product to be delivered without effecting delivery of the injectable product, clutch means in engagement with said rod for restricting rotation of said rod in a second and opposite direction; and a clutch disengaging means for selectively disengaging said clutch means, thereby permitting rotation of said knob means in said second direction while said cartridge is attached to said injector means to cause said rod to move axially toward said injector means to reduce the first distance of axial advancement of said rod thereby reducing the set dosage of injectable product to be delivered, wherein said rod is axially advanceable a second distance upon axial force being applied to said knob means to engage and axially advance said plunger to effect delivery of the set dosage of injectable product.

12. The device of claim 11, including a digital display means operatively coupled to said knob means for providing a visual dosage indication that increments and decrements as said knob rotates respectively in the first and second directions.

13. The device of claim 11, wherein said rod is threadedly coupled to said knob means.

14. The device of claim 11, including means for disengaging said clutch means when the cartridge is removed from said injector.

15. An injector device for injecting a product contained in a cartridge attached to the injector, said cartridge including a plunger therein, comprising:
    a housing;
    a drive mechanism disposed in said housing and including a dosage device having a control knob and a rod coupled to said dosage device such that upon rotation of said knob, said rod is axially advanceable a first distance to establish a set dosage of injectable product to be delivered without effecting delivery of the injectable product;
    a clutch mechanism disposed in said housing and comprising a rotatable piece that is connected to said dosage device for rotation therewith and a locking seat in engagement with said rotatable piece and being configured to restrict rotation of said rotatable piece, and hence said dosage knob, to a first direction only while the injector is attached to a cartridge; and a disengaging mechanism for selectively disengaging said locking seat from said rotatable piece thereby permitting rotation of said dosage device in a second and opposite direction while the injector is attached to the cartridge to permit an overdose measurement to be dialed back to a desired dosage, wherein said rod is axially advanceable a second distance upon axial force being applied to said knob to engage and axially advance said plunger to effect delivery of the set dosage of injectable product.

16. In a medication dispensing device for measuring and injecting a desired dosage of injectable product into a patient, a method for reducing an excess dosage of measured product, the method comprising the steps of:

attaching a cartridge containing an injectable product therein to an injector including a dosage knob and an axially advanceable rod;

rotating the knob in a first direction only to cause the rod to axially advance into the cartridge a first distance to establish a set dosage of injectable product to be delivered without effecting delivery of the injectable product;

engaging a clutch-deactuating mechanism;

rotating the dosage knob in a second and opposite direction until the rod has been axially retracted within the cartridge a sufficient distance to reduce the set dosage to be injected; and releasing the clutch-deactuating mechanism thereby preventing rotation of the dosage knob in the second direction while the cartridge is attached to the injector.

* * * * *